United States Patent [19]
Noffsinger et al.

[11] Patent Number: 5,663,044
[45] Date of Patent: Sep. 2, 1997

[54] METHODOLOGY FOR COLORIMETRICALLY DETERMINING THE CONCENTRATION OF WHITE BLOOD CELLS IN A BIOLOGICAL FLUID

[75] Inventors: James Noffsinger, Goshen; Michael J. Pugia; Melvin D. Smith, both of Granger, all of Ind.

[73] Assignee: Bayer Corporation, Elkhart, Ind.

[21] Appl. No.: 606,871

[22] Filed: Feb. 26, 1996

Related U.S. Application Data

[63] Continuation of Ser. No. 339,797, Nov. 15, 1994, abandoned.

[51] Int. Cl.$^6$ .............................. C12Q 1/00; C12Q 1/34; C12Q 1/37; G01N 33/53
[52] U.S. Cl. .............................. 435/4; 435/7.24; 435/18; 435/24; 435/19; 435/23; 435/963; 435/970; 435/283.1; 435/287.1
[58] Field of Search ................................ 435/4, 7.24, 18, 435/24, 19, 23, 963, 970, 283.1, 287.1

[56] References Cited

U.S. PATENT DOCUMENTS 4,554,236  11/1985  Bentley et al. .............................. 435/4

FOREIGN PATENT DOCUMENTS 0157326   9/1985   European Pat. Off. .
83032254  9/1983   WIPO .

OTHER PUBLICATIONS

Kutter et al, "J. Clin. Chem. Clin. Biochem", vol. 25, 1987, pp. 91–94. (Month of Publication Not Available; Please Print).

Benoist et al, "Analytical Biochemistry", vol. 187, pp. 337–344, 1990. (Month of Publication Not Available; Please Print).

Brown et al, "J. of Chromatography", p. 169 (1979) pp. 407–408. (Month of Publication Not Available).

Miller et al, "J. of Biochem & Biophysical Meth", 3 (1980) pp. 345–354.

Bardi et al, "J. Inst. Brew.", vol. 99, pp. 385–388, Oct. 1993.

*Primary Examiner*—John Kight
*Assistant Examiner*—Louise Leary
*Attorney, Agent, or Firm*—Roger N. Coe

[57] ABSTRACT

A composition, method and test device for determining the presence of leukocytes, esterase or protease in a test sample are disclosed. The composition comprises an ester which is hydrolyzed in the presence of leukocyte, esterase, or protease to form a reaction product which couples with a diazonium salt to produce a detectable color change. The composition further comprises the salt of an alkaline earth metal which stabilizes the composition during manufacture and prevents the occurrence of false or background color change due to reactivity of the diazonium salt in the absence of leukocyte, esterase or protease.

21 Claims, No Drawings

METHODOLOGY FOR COLORIMETRICALLY DETERMINING THE CONCENTRATION OF WHITE BLOOD CELLS IN A BIOLOGICAL FLUID

This application is a continuation of application Ser. No. 08/339,797, filed Nov. 15, 1994 now abandoned.

FIELD OF THE INVENTION

The present invention is directed to a means for colorimetrically determining the presence of leukocytes in a biological fluid. The invention more particularly concerns the use of an alkaline earth metal in a reagent composition formulated to undergo a color change in the presence of esterase or protease.

BACKGROUND OF THE INVENTION

The presence of an abnormally high level of leukocytes in a patient's urine or other bodily fluids is possibly indicative of such pathological conditions as kidney or urogenital tract infection or other dysfunction. Accordingly, accurate urinary leukocyte information can be an invaluable tool to the physician in diagnosis and treatment of such pathologies.

Traditionally, the medical profession has relied on visual determination techniques to count leukocyte population in urine sediment or uncentrifuged urine, a process requiring expensive equipment such as a centrifuge and microscope, as well as inordinate time expenditure on the part of the clinician. Moreover, the traditional techniques suffer from the disadvantage that only intact cells are detected. Leukocytes in the urinary system are subject to conditions which favor extensive cell lysis. For example, it is known that in urines of abnormally high pH, leukocyte half life can be as low as 60 minutes. Since lysed cells escape detection in visual examination techniques, erroneously low determinations and false negatives can result.

In the more recent past, the medical profession has relied on detecting hydrolytic enzymes contained within leukocytes rather than counting the intact cells themselves. Methods for colorimetrically determining the presence of leukocytes through the measurement of hydrolytic esterases and proteases contained within the cells utilize compositions which include chromogenic esters which when hydrolyzed by esterase or protease, produce a colored alcoholic product. Many of these compositions also include accelerator compounds and diazonium salt coupling agents.

Thus, there exists in the prior art a body of references which disclose the use of certain esters which, when cleaved by enzymatic activity, result in the formation of colored or other detectable species. British Patent No. 1,128,371 ('371) discloses the use of indoxyl and thioindoxyl esters as useful chromogens in detecting hydrolytic enzymes in body fluids. The enzymes cleave the ester to generate free indoxyl, which subsequently oxidizes to form the dimeric product indigo, a readily observable blue dye. Such activity is said to be due to, among other enzymes, cholinesterase. The patent '371, also teaches that, in addition to the indoxyl portion of the ester substrate, the acid radical is chosen with particular reference to the enzyme to be detected. For example, it is stated that the acid radical can be acetate, laureate or stearate for detection of esterase or lipase, respectively. For detecting enzymes such as phosphatase or sulfatase the acyl radical can be an inorganic radical. Thus, '371 teaches the use of chromogenic esters as substrates for determining esterolytic enzymes, such esters comprising indoxyl or thioindoxyl as the alcoholic moiety of the ester the acyl moiety being tailored to the particular enzyme to be determined.

The effect of careful acyl radical selection is nowhere more clearly exemplified than in two references which demonstrate esterase specificity for esters in which the acyl radical comprises an N-protected amino acid or peptide. Janoff et al., Proc. Soc. Exper. Biol. Med. 136:1045–1049 (1971), teaches that alanine esters are specific substrates for esterase obtained from human leukocytes. Specifically, Janoff teaches that an extract of human leukocyte granules is capable of hydrolyzing N-acetyl-L-alanyl-L-alanyl-L-alanine methyl ester. Moreover, L-alanine-p-nitrophenyl ester was similarly hydrolyzed to yield the yellow p-nitrophenol colorform.

Similarly, Sweetman et al., Jour. Hist. Soc., 22:327–339, teaches the use of 1-naphthyl N-acetyl-DL-alanine, 1-naphthyl N-acetyl-L-alanyl-L-alanyl-L-alanine and 1-naphthyl butyrate to demonstrate the presence of esterase.

U.S. Pat. No. 4,278,763, assigned to Boehringer Mannheim GmbH, combines these teachings in arriving at the indoxyl or thioindoxyl esters of amino acids or peptides as still another example of a traditional chromogenic substrate for leukocytic esterase activity. Like Janoff and Sweetman, the Boehringer patent teaches the equivalence of protease and esterase in their esterolytic penchants.

It is known that ester hydrolysis reactions can be activated by the presence of many nucleophilic agents, including a myriad of alcohols. Thus, the rate of hydrolysis of phenyl acetate and p-nitrophenyl acetate by esterase is increased 2.5 to 5.5 times upon addition of methanol or butanol. Greenzaid and Jencks, Biochemistry, 10(7), 1210–1222 (1971). Moreover, the effect increases with the length of the n-alkyl group. Wynne and Shalatin, Eur. J. Biochem 31:554–560 (1972).

In particular, this activation effect of alcohols has been observed with esters of amino acids. p-Nitrophenyl-N-acetyl-L-alaninate hydrolysis is activated (accelerated) by the presence of methanol. Fastrez and Fersht, Biochemistry, 12(11), 2025–2034 (1973). High molecular weight alcohols increase the rate of esterase-induced hydrolysis of p-nitrophenyl-t-BOC-L-tyrosinate. Ashe and Zimmerman, Biochem. and Biophys. Res. Comm., 75(1), 194–199 (1977). The disclosure of U.S. Pat. No. 4,299,917 describes other known ester hydrolysis activators such as certain metal complexes, pyridine derivatives and imidazoles.

Also known in the art is the use of certain diazonim salts to couple with phenols and pseudophenols to produce azo dyes. Martinet and Dornier Compt. Rend., 170, 592 (1920). Such a technique is used in an esterase analysis whereby indoxyl esters are hydrolyzed via esterase to produce indoxyl, which is in turn coupled with a diazonium salt to form the corresponding azo dye. Holt and Hicks, J. Cell Biol. 29, 261–366 (1966); Gossrau, Histochemistry, 57, 323–342 (1978); West German Offenlegungschrift No. 30 17 721, filed May 9, 1980.

The diazonium salts known for use as coupling agents in a composition for detecting leukocytes, esterase, or protease rely upon an exogenous anion to counter the diazo cation. Moreover, the formulations discussed thus far each suffers, to at least some extent, from interference or inaccuracy due to the presence of phenolic or other compounds present in the sample which are capable of reacting with the diazonium salt. Such interference can result in false negative assays.

Skjold (U.S. Pat. No. 4,637,979) combined the use of a chromogenic ester, diazonium salt coupling agent, and accelerant into an easy to use dip-and-read test composition and device. In the presence of leukocyte, esterase, or protease, the ester is hydrolyzed to an acid and a phenol. The phenol is then free to couple with the diazonium to produce a color change.

Skjold's composition and test device, however, did not consistently provide accurate results at the basic pHs that most favored enzyme mediated hydrolysis and subsequent coupling of the diazonium with the liberated phenol. Specifically, the color change results were inaccurate at higher pHs because while hydrolysis and diazonium coupling increased with increasing basicity of the reaction mixture, so also did background reactivity of the diazonium with other components in the mixture. Thus, at pHs around 8.8–9.0 color change frequently resulted even in the absence of enzyme. It has been suggested that these background color changes occur with increasing pH of the reaction mixture due to increased nucleophilic attack on the diazonium salt by hydroxide ions. Clearly, there is a need for a reagent composition for detecting leukocytes, esterase or protease which can be utilized at a pH which promotes efficient enzyme mediated hydrolysis and diazo coupling but at the same time promotes diazonium stability in the absence of such enzymes. Additionally, there is a need for a reagent composition in which the diazonium salt remains stable during manufacture.

Diazonium compounds are used in a variety of applications in medicine and industry. Thus, various attempts have been made to try to stabilize such compounds against nucleophilic attack and other types of degradation. Stabilization attempts have included the use of compounds such as organic base, surfactants, organic borates, antioxidants, acid stabilizers, and zinc chloride. None of these approaches was, however, designed to stabilize diazonium salts in a reagent composition formulated to detect leukocytes. Furthermore, none has proven successful in such a composition. Zinc chloride is not effective because it reduces the reactivity of the esterase and protease enzymes. Acid stabilizers do not work because the enzyme detection composition must be basic in order to promote diazonium reactivity and enzyme activity. Surfactants, anti-oxidants, and organic borates were tested but had little effect in stabilizing the diazonium.

Given the limitations of the prior known art, there is a clear need for a method of stabilizing the diazonium against nucleophilic attack and at the same time allow for a composition pH of between 8.8–9.0 in order to promote efficient diazo coupling in the presence of enzyme.

SUMMARY OF THE INVENTION

The present invention provides novel compositions, test devices, and methods for assaying a sample of bodily fluid for leukocytes by detecting the presence of hydrolytic enzymes such as esterases and proteases contained in such cells. The compositions of the invention comprise esters which when hydrolyzed by enzyme yield a product which can couple with a diazonium salt to produce a detectable color change. The compositions further comprise the salt of an alkaline earth metal. The metal salt stabilizes the diazonium, thus, reducing background reactivity. This allows for a more basic composition pH which promotes increased diazonium reactivity in the presence of enzyme.

The invention also provides test devices for determining the presence of leukocyte, esterase or protease. The test devices comprise a carrier matrix onto which the composition is impregnated. The carrier matrix may be made of suitable materials such as filter paper, glass, felt or wood.

The present invention further provides for a method of assaying bodily fluids for leukocyte cells, esterase or protease. The method comprises contacting a test sample with the reagent composition or test device incorporating the composition, then observing and measuring a detectable response such as a color change.

DESCRIPTION OF THE PREFERRED EMBODIMENT

The present invention provides for a composition for determining the presence of leukocyte, esterase or protease in a test sample. More specifically, the invention provides for a composition which allows for efficient detection of analyte while reducing background reaction. The composition is composed of an ester, a diazonium salt, and an alkali earth metal salt. While there is great latitude in choosing these ingredients, there are preferred embodiments of each which produce maximized results, i.e., a high degree of detectable response developing in a short time. This optimization can be still further promoted by including an accelerator in the composition. The expression "detectable response" is intended herein as meaning a change in or occurrence of a parameter in a test means system which is capable of being perceived, either by direct observation or instrumentally; and which is a function of the presence of a specific analyte in an aqueous test sample. Preferred detectable responses are the change in or appearance of color, fluorescence, reflectance, chemiluminescence and infrared spectra.

The composition contains art ester of an aromatic or pseudoaromatic phenol and an acid. Moreover, the ester is one which is capable of being catalytically hydrolyzed in the presence of leukocytes, esterase or protease to yield the phenol or pseudophenol, which is then free to couple with the diazo zwitterion.

Some esters suitable for use with the invention include indoxyl acetate, indoxyl butyrate, indoxyl laureate, indoxyl stearate, indoxyl ester of a N-blocked amino acid or peptide and thioindoxyl analogs thereof. Also included are p-nitrophenol-N-tosyl-L-alaninate, α-naphthyl and alaninate. A preferred ester is a lactate ester. The lactate ester is hydrolyzed by the leukocyte esterase to provide a hydroxypyrrole compound which in turn can interact with the diazonium salt to form an azo dye. The lactate esters of the present invention are readily hydrolyzed by esterase to generate a measurable color transition or other detectable response within about 60 to about 120 seconds.

A preferred composition of the present invention, which is capable of detecting esterase and therefore is capable of detecting leukocyte cells, comprises a lactate ester having the general structural formula (I)

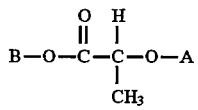

(I)

wherein A is an alcohol blocking group and B is a moiety capable of providing a detectable response, preferably a chromogenic response, when the lactate ester of structural formula (I) is hydrolyzed to generate the compound B—OH. The lactate ester can be the D-form, the L-form or a racemic mixture of the D and L-forms. The L-form is preferred.

The moiety B—O— of the compound of structural formula (I) is defined as the residue of a compound B—OH. The moiety. B—O— therefore can be the residue of a substituted or unsubstituted pyrrole, thiophene or furan, for example. Other exemplary compounds having a residue B—O— include, but are not limited to, an azoresorcinol ester, a phenoxy ester (with an oxidative coupler), a leukoindophenol ester, an azo dye ester, 5-(4-hydroxy-3,5- dimethoxyphenylmethylene)-2-thioxothiazoline-3-acetic acid, a 2-substituted-6-hydroxy-benzothiazole derivative disclosed in WO 90/00618 and EP 399 490, a ω-nitrostyryl ester, a resorufin ester, an acridinone, a merocyanine, an 8-hydroxy-2H-dibenz-(b,f)azepin-2-one, a dibenzo azepinone, a dibenzothiazepinone, a coumarin ester, or a chemiluminescent compound disclosed in EP 254 051, incorporated herein by reference.

A preferred lactate ester has the general structural formula (II)

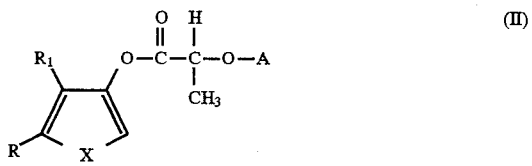

wherein A is an alcohol blocking group, X is O, S or $NR^2$, R is aryl or lower alkyl, $R_1$ is hydrogen or lower alkyl, and $R_2$, is hydrogen, lower alkyl or aryl. The lactate ester of general structural formula (II) is hydrolyzed by the enzyme leukocyte esterase to generate a hydroxy-compound, such as a hydroxy-pyrrole.

The lactate ester (II) is present in a reagent composition in a concentration of about 0.5 to about 2 mM (millimolar), and preferably about 0.8 to about 1.5 mM. Within this concentration range, a sufficient mount of lactate ester is present in the reagent composition to provide a sufficient color transition or other detectable response to detect trace mounts of leukocyte cells.

The term "lower alkyl," as used herein, is an alkyl moiety containing one to about six carbon atoms. Exemplary, but nonlimiting, lower alkyl groups include methyl, ethyl, n-propyl, isopropyl, n-butyl, sec-butyl, tert-butyl and all isomers of pentyl and hexyl. The lower alkyl group can be unsubstituted, or the lower alkyl group can be substituted, provided the substituent does not interfere with the ability of the composition or test device to detect leukocyte cells, esterase or protease. Exemplary, but nonlimiting, substituents on the alkyl group are alkoxy having one to six carbon atoms, halo, nitro, aryl, and amino.

The identity of the alcohol blocking group, i.e., A, of the lactate ester of general structural formula (I) is not particularly limited, and can be selected from essentially any blocking group typically used to protect an alcohol moiety.

The alcohol blocking group A typically is the residue of a sulfonyl chloride or a carboxylic acid chloride (i.e., an acyl chloride) and has the structural formula (III) or (IV)

wherein $R_3$ is an alkyl group having three to about 22 carbon atoms, and preferably 3 to about 6 carbon atoms, or $R_3$ is an aryl group. When $R_3$ is an aryl group, the alkyl group can be functionalized, e.g., methoxy-succinyl.

As used herein, the term "aryl" with respect to R, $R_2$, and $R_3$ means any aromatic ring system. Nonlimiting examples of the term "aryl" include 5- and 6- membered aromatic ring systems like pyrrolyl, phenyl and pyridyl, as well as fused aromatic ring systems, like naphthyl. The aromatic ring system can be heterocyclic or carbocyclic, and can be substituted or unsubstituted, provided that the substituent groups do not interfere with ability of the chromogenic lactate ester to hydrolyze in the presence of leukocyte cells, esterase or protease. Exemplary, but nonlimiting substituent groups are alkyl, halo, acyl, aryl, hydroxy, alkoxy, sulfuryl and amino. The aryl group preferably is a phenyl group, either unsubstituted or substituted with a relatively nonreactive group, such as a halo group or an alkyl or alkoxy group having one to about 10 carbon atoms.

Exemplary, but nonlimiting, alcohol blocking groups are residues of p-toluenesulfonyl chloride (tosyl chloride or TsCl), n-propylsulfonyl chloride (n-PrSO2Cl ), benzoyl chloride (PhCOCl), carbomethoxyethane sulfonyl chloride and thiophene sulfonyl chloride. Numerous other specific alcohol blocking groups are known to those skilled in the art and can be used as the A component of the present lactate esters. For example, numerous alcohol blocking groups are disclosed in T. W. Greene et al., Protecting Groups in Organic Chemistry, 2d Ed., (1991), incorporated herein by reference.

A preferred alcohol blocking group A has the structural formula (III) and includes the sulfonyl moiety. To achieve the full advantage of the present invention, the alcohol blocking group of structural formula (III) has a phenyl group as $R^3$, wherein the phenyl group is substituted with a methyl or a methoxy moiety.

A preferred lactate ester of the present invention is a chromogenic compound having the structural formula (V)

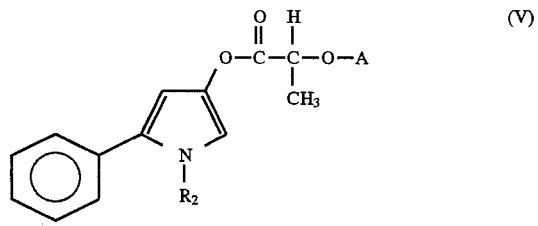

which is the L-form of a lactate ester of general structural formula (II), wherein X is $NR^2$, R is phenyl and $R_1$ is hydrogen. A and $R_2$ have the same meanings as previously described. In a more preferred embodiment, the chromogenic lactate ester has structural formula (VI):

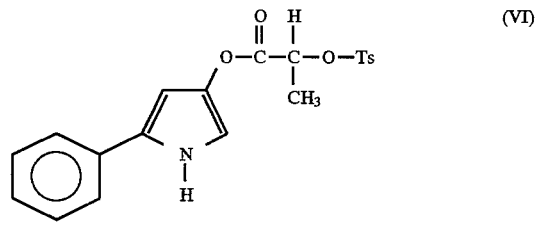

wherein $R_2$ is hydrogen and A is p-toluenesulfonyl (i.e., Ts), i.e., the L-form of the lactate ester of structural formula (II) wherein X is NH, A is Ts, R is phenyl and $R^1$ is H.

The method of synthesis of preferred lactate esters is described in detail in U.S. patent application Ser. No. 293,723, filing date Aug. 22, 1994, now U.S. Pat. No. 5,464,739, assigned to Miles Inc of Indiana.

The composition of the present invention can include, in addition to the ester, various accelerators. The expression "accelerator" relates to any compound which serves to increase the rate of hydrolysis of the chromogenic esters described herein. Included are such chemically diverse substances as pyridine, imidazole and their derivatives; certain metal complexes; and alcohols. Suitable alcohols have from 1 to about 15 carbon atoms. Linear alcohols are preferred over branched chain alcohols, although the latter are included within the scope of the invention. Alcohols having 8–15 carbon atoms are particularly useful in increasing esterase and protease catalyzed hydrolysis of esters discussed herein. Decanol, undecanol, and dodecanol are specifically preferred for use with this invention primarily because of their low volatility as compared with alcohols of low molecular weight.

The composition also includes a diazonium salt as a coupling agent. The diazonium salt coupling agent has a general structural formula

wherein Ar is an aryl group. More particularly, the diazonium salt typically is an aromatic diazonium salt having the general structural formula:

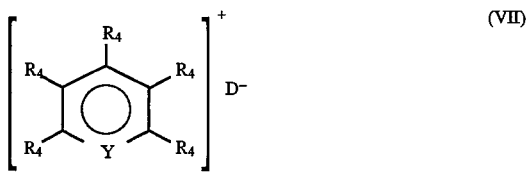

wherein $R_4$ is individually hydrogen, lower alkyl or aryl, or wherein two adjacent $R_4$ groups together form a fused ring system, with the proviso that one of $R_4$ is $-N^+\equiv N$, i.e., diazonium; Y is N or $CR_5$, wherein $R_5$ is hydrogen or lower alkyl; and D is an anion, such as chloride, bromide or other suitable counterion for the diazonium moiety. Another preferred diazonium salt has the structure

wherein F is hydrogen, lower alkyl or hydroxy; D is a covalently bound anion: G. individually is hydrogen, lower alkyl or aryl, or both G groups taken together from a fused ring system.

The term "fused ring system," as used herein, means two or more aromatic rings that share a pair of carbon atoms.

A zwitterionic diazonium salt is a preferred coupling agent. The zwitterionic diazonium compound is a species of diazonium salt wherein the counterion (i.e., the anion) of the diazonium moiety is covalently bound to the ring system. Examples of such anions include, but are not limited to, sulfonate ($SO_3$), carbonate ($CO_2$) and phosphonate ($PO_3$).

Various diazonium salts are disclosed in Skjold et al. U.S. Pat. No. 4,637,979; Hugh et al. U.S. Pat. No. 4,806,423; and Hugl et al. U.S. Pat. No. 4,814,271, incorporated herein by reference. Specific, nonlimiting examples of diazonium salts useful in the composition and method of the present invention are 1-diazo-2-naphthol-4-sulfonate and 1-diazophenyl-3-carbonate. Other nonlimiting examples of diazonium salts are 4-diazo-3-hydroxy-1-naphthylsulfonate (DNSA), 4-diazo-3-hydroxy-7-nitro-1-naphthylsulfonate (NDNSA), 4-diazo-3-hydroxy-1,7-naphthyldisulfonate, 2-methoxy-4-(N-morpholinyl) benzene diazonium chloride, 4-diazo-3-hydroxy-7-bromo-1-naphthylsulfonate and 4-diazo-3-hydroxy-7-[1, oxopropyl]-1-naphthylsulfonate.

When the ester of the composition is hydrolyzed by leukocyte, esterase or protease, a hydroxy-pyrrole is liberated which can interact with the diazonium salt to form a brilliant azo dye and color change.

The composition of the present invention also contains the salt of an alkaline earth metal. Preferred alkaline earth metals include magnesium, calcium, and barium. A preferred salt is magnesium sulfate but all alkaline earth metals are expected to perform similarly. The alkaline earth metal stabilizes the diazonium against attack during manufacture and storage of the reagent composition and also reduces background reactivity of the diazonium during testing of bodily fluids. The metal salt reduces background color change in both instances. Background color change is that which occurs in the absence of enzyme. It has been speculated that such color change is caused by nucleophilic attack of the diazonium salt by components of the reaction mixture and from other extraneous sources during the manufacturing process.

Table 1 more particularly demonstrates that $MgSO_4$ stabilizes the reagent composition against background color change.

The data presented in column 4 of the table below shows that when $MgSO_4$ is added to the first dip solution formulated as described previously, there is less color change (background) in the absence of leukocyte, esterase or protease. $MgSO_4$ likely forms metal hydroxides with excess $OH^{13}$ s in the reaction mixture. These metal hydroxides are less nucleophilic than sodium hydroxide, and therefore, less reactive towards the diazonium.

TABLE 1

Stabilization of the Diazonium in the Absence of Leukocytes and During Storage Conditions

| Formulation | Storage Condition Time | Temp. | Reactivity After Dipping in Negative Test Solution | Reactivity After Dipping in Positive Test Solution |
| --- | --- | --- | --- | --- |
| Control | Initial | 23° | 954 | 686 |
| $MgSO_4$ | Initial | 23° | 973 | 610 |
| Control | 1 week | 23° | 960 | 713 |
| $MgSO_4$ | 1 week | 23° | 975 | 650 |
| Control | 1 week | 60° | 875 | 744 |
| $MgSO_4$ | 1 week | 60° | 914 | 729 |
| $MgCl_2$ | Initial | 23° | 968 | 675 |

The numbers in column 4 represent percent reflectance of the composition as measured by a CLINITEK™-200 Urine Chemistry Analyzer, produced by Miles Inc. of Indiana. Percent reflectance of the composition coated reagent strip is measured at a wave length of 570 nanometers, divided by the reflectance measured at a standard of 690 nanometers and multiplied by 1000. Since percent reflectance is inversely related to color change, the smaller the percentage reflectance number the deeper the color change and thus the greater false positive in the absence of enzyme.

The data presented in column 5 of Table 1 demonstrates that metal salts stabilize the reagent composition during storage. The detection of leukocyte, esterase and protease is enhanced when less of the diazonium salt is degraded during storage. Specifically, the numbers in column 5 show reactivity of the composition in the presence of 42 leukocyte cells/ml of test solution. As can be seen, after one week of storage, there is more color change in the presence of leukocytes when $MgSO_4$ is in the reagent mixture. Again, since percent reflectance is measured, a lower number means more color change in the presence of leukocytes.

Table 2 shows the effect of diazonium stabilization by $MgSO_4$ after a simulated four week shelf life at 60° C.

TABLE 2

Diazonium Stability Data After 4 Week Shelf Life

| | Reactivity After Dipping in Positive Test Solution |
|---|---|
| Control (pH 8.8) | 673 |
| MgSO₄ (pH 8.8) | 596 |
| MgSO₄ (pH 8.95) | 557 |

CLINITEK ™ -200 values are % reflectance at 570 nm/% reflectance at 690 nm × 1000.
42 leukocyte cells/ml are present in the test solution.

In the presence of 42 cells/ml of test solution, reagent compositions containing MgSO₄ exhibit greater Color change as compared to the control solution. This color change is most pronounced at pH 8.95, a pH optimum for enzyme hydrolysis and diazonium coupling.

In addition to stabilizing the diazonium during storage, it is also likely that the alkaline earth metal ion absorbs moisture generated in the drying oven. Moisture likely causes background color change due to water molecules reacting with the diazonium salt. Table 3 demonstrates that there is less background color change when the composition is exposed to high humidity when MgSO₄ is present in the reagent composition.

TABLE 3

Magnesium Sulfate Added to the Second Mix

| Formulation | Humidity Condition % RH | Temp. F. | CLINITEK-200 Reactivity in the Absence of Leukocyte |
|---|---|---|---|
| Control | 20% | 72° F. | 956 |
| Control | 45% | 72° F. | 906 |
| Control | 55% | 72° F. | 860 |
| 4 mM MgSO₄ | 30% | 72° F. | 957 |
| 4 mM MgSO₄ | 55% | 71° F. | 960 |

Thus, it seems that addition of an alkaline earth metal salt to the reagent composition of this invention enhances leukocyte detection in two fundamental ways. First, it is believed that the metal salt shields the diazonium against nucleophilic attack by extraneous components in the reagent composition during the testing of bodily fluids. Thus, color change in the absence of leukocytes (background) is reduced. Second, the metal salt is believed to absorb moisture in the drying phase of manufacture and to prolong shelf life of the composition and test device during storage. Since less diazonium is degraded, the test composition is more sensitive to leukocytes.

The composition of the present invention may include a buffer. The buffer is a compound which, when contacted with an aqueous test sample, provides a suitable pH for the reaction. Preferably, the buffer is capable of producing a pH in the range of about 8.8 to 9.0. As discussed previously, this later pH range allows for a most dramatic color change in the presence of leukocyte, esterase, or protease because it facilitates hydrolysis by esterase and protease and diazonium coupling. The metal salt protects against background color change which is color change in the absence of leukocyte, esterase, or protease.

A buffer can be included in the reagent composition of the present invention in a concentration of about 200 to about 600 mM, although in particular situations the concentration of the buffer can be above or below this range.

Therefore, a reagent composition of the present invention is buffered to a suitable pH with a buffer such as carbonic acid; BICINE; CHES; borate; phosphate: 2,2-bis (hydroxymethyl)-2,2', 2"-nitrilotriethanol; 3,3-dimethylglutaric acid; 3-N-morpholinopropanesulfonic acid (MOPS); 1,3-bis[tris(hydroxymethyl)methyl-amino] propane (Bis-TRIS); tri(hydroxymethyl)aminomethane (TRIS); tris(hydroxymethyl)aminomethane-maleic acid (TRIS-maleate); tris(hydroxymethyl) aminomethane-malonic acid (TRIS-malonate); 3-N-(trishydroxymethyl) methylamino-2-hydroxypropanesulfonic acid (TAPSO); 2-( [tris(hydroxymethyl)methyl]amino) ethanesulfonic acid (TES); N-2-hydroxyethylpiperazine-N'-2-ethanesulfonic acid (HEPES); and other buffers well known in the art, or combinations thereof. A preferred buffer is boric acid-NaOH.

The composition described above can be used in determining the presence of leukocyte, esterase or protease. Alternatively, the composition can be incorporated into a carrier matrix to form a test device, thereby providing a tool for rapid, reliable estimation of the presence of the analyte. The carrier matrix is usually, but not necessarily, a porous substance such as filter paper. Other well known forms of carrier matrix materials are felt, porous ceramic strips, and woven or matted glass fibers (U.S. Pat. No. 3,846,247). Also contemplated are the use of wood, cloth, sponge material and argillaceous substances (U.S. Pat. No. 3,552,928). Alternatively, the carrier matrix can be non-porous, such as various polymeric films, glass and the like. All such carrier matrix materials are feasible for use in the present invention, as are others. It has been found that filter paper is especially suitable.

In a preferred method of preparing the device, a piece of filter paper is wetted with an aqueous solution of the buffer and aqueous salt of an alkaline earth metal. This first-dip solution can also contain various processing excipients such as a detergent, a sizing agent such as polyvinylpyrrolidone, and other inert ingredients.

The impregnated filter paper is then dried and wetted with a second-dip solution, in acetone and DMSO or other nonaqueous solvents, the diazonium salt and, if desired, the accelerator or additional buffers. The twice-impregnated paper is then dried a second time, thus forming a test device sensitive to the presence of leukocytes or other analytes. It is also possible to impregnate the filter paper utilizing a one-dip solution containing all the necessary reagents.

A preferred recipe for the reagent composition is listed in Table 4.

TABLE 4

Leukocyte Detection Reagent Composition

| Ingredient | Function | Preferred Conc. Used | Allowable Range |
|---|---|---|---|
| 1st Application | | | |
| Water | Solvent | 1000 mL | — |
| Magnesium sulfate | DNSA stabilizer | 14.6 g | 1–30 g/L |
| Bio-Terge AS40 | Surfactant | 2 g | 0–4 g/L |
| Boric acid | Buffer | 24.7 g | 5–35 g/L |
| PVP | Polymer | 20.0 g | 5–50 g/L |
| 2nd Application | | | |
| MOP | Solvent | 955 mL | — |
| DMPU | Solvent | 30 mL | 10–60 mL |
| DNSA | Diazonium indicator | 0.174 g | 0.050–0.5 g/L |
| PPTA | Enzyme substrate | 0.422 g | 0.10–0.8 g/L |

TABLE 4-continued

Leukocyte Detection Reagent Composition.

| Ingredient | Function | Preferred Conc. Used | Allowable Range |
|---|---|---|---|
| Decanol | Enzyme activator (accelerator) | 15 mL | 5–40 mL/L |
| Boric Acid | Buffer | 0.5 g | 0–3.0 g/L |

DNSA = 1-diazo-2-naphthol-4-sulfonic acid
PPTA = 2-hydroxy-5-phenyl-pyrrole-N-tosyl-L-alanine ester The dried, reagent-bearing carrier matrix can be mounted on a backing material if desired. Thus, in a preferred embodiment of the test device, a filter paper carrier matrix is incorporated with the composition as described, supra, the matrix being affixed to one side to an elongated piece of transparent polystyrene film. The matrix is secured to the film by any suitable means, such as double faced adhesive tape (Double Stick® available from 3M Company), the other end of the polystyrene film serving as a handle. In use, such a device is held by the free end of the polystyrene film backing material and the matrix end is immersed into the test sample (e.g., urine) and quickly removed. Any color formation or other detectable response is observed after a predetermined time and compared with a reference standard corresponding to responses to known concentrations of leukocytes or other analyte having esterase or protease activity. It has been found that an incubation time of about 1–3 minutes is usually sufficient to enable color development to occur in the reagent-containing filter paper.

What is claimed is:

1. A composition for determining the presence of an analyte selected from the group consisting of leukocyte, esterase and protease in a test sample, the composition comprising a mixture of the following components:

a diazonium salt, an ester subject to hydrolysis in the presence of leukocyte, esterase or protease, and at least 8.3 mM of an added salt of an alkaline earth metal.

2. The composition of claim 1, wherein said alkaline earth metal salt is a salt of magnesium, calcium, or barium.

3. The composition of claim 2, wherein said alkaline earth metal salt is a salt of magnesium.

4. The composition of claim 3, wherein said salt is $MgSO_4$.

5. A composition for determining the presence of an analyte selected from the group consisting of leukocyte, esterase and protease in a test sample, the composition comprising a mixture of the following components:

a diazonium salt, an ester subject to hydrolysis in the presence of leukocyte, esterase or protease, and at least 8.3 mM of an added salt of an alkaline earth metal, wherein a pH optimum of the composition facilitates diazonium coupling in the presence of leukocyte, esterase or protease and minimizes background diazonium coupling and color change.

6. The composition of claim 5, wherein the pH optimum is from about 8.8 to 9.0.

7. The composition of claim 6, wherein the pH optimum is about 8.95.

8. The composition of claim 5, wherein said ester is a lactate ester having the structure, formula I:

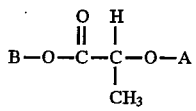

wherein A is an alcohol blocking group, and B is moiety capable of providing a detectable response, preferably a chromogenic response when said lactate ester of formula I undergoes hydrolysis to generate compound B—OH.

9. The composition of claim 8, wherein the compound B—OH is selected from the group consisting of a pyrrole, a thiophene, a furan, an azoresorcinol, a phenol, a leukoindophenol, an azo dye, 5-(4-hydroxy-3-dimethoxyphenylmethylene)-2-thioxothiazoline-3-acetic acid, a2-substituted-6-hydroxy-benzothiazole derivative, a ω-nitrostyryl ester, a resorufin, an acridinone, a merocyanine, an 8-hydroxy-2H-dibenz-(bf)azepin-2-one, a dibenzo azepinone, a dibenzothiazepinone, a coumarin ester, and mixtures thereof.

10. The composition of claim 5, wherein said diazonium salt has the structure, formula VII:

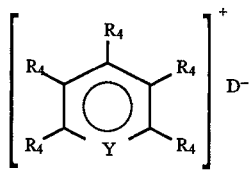

wherein $R_4$ is individually hydrogen, lower alkyl or aryl, or wherein two adjacent $R_4$ groups together form a fused ring system, with the proviso that one of $R_4$ is $N^+{\equiv}N$; Y is N or $CR^5$, wherein $R^5$ is hydrogen or lower alkyl; and $D^-$ is an anion having a charge of negative 1.

11. The composition of claim 5, wherein said diazonium salt has the structure, formula VIII:

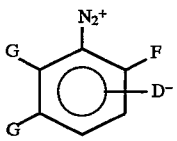

wherein F is hydrogen, lower alkyl or hydroxy; D is an anion having a charge of negative 1; G is individually hydrogen, lower alkyl or aryl, or both G groups taken together from a fused ring system.

12. The composition of claim 5, wherein said diazonium salt is selected from the group consisting of 1-diazo-2-naphthol-4-sulfonate, 1-diazophenyl-3-carbonate, 4-diazo-3-hydroxyl-1-naphthylsulfonate, 4-diazo-3-hydroxy-7-nitro-1-naphthylsulfonate, 4-diazo-3-hydroxy-1,7-naphthyldisulfonate, 2-methoxy-4-(N-morpholinyl)benzene diazonium chloride, 4-diazo-3-hydroxy-7-bromo-1-naphthylsulfonate, 4-diazo-3-hydroxy-7-cyano-1-naphthylsulfonate, 4-diazo-3-hydroxy-7-[1-oxopropyl]-1-naphthylsulfonate, and mixtures of said diazonium salts.

13. The composition of claim 1, wherein said composition additionally comprises an accelerator.

14. The composition of claim 13 in which the accelerator is an alcohol having about 8–15 carbon atoms.

15. A test device for determining the presence or concentration of leukocytes, esterase or protease, in a test sample, said test device comprising a carrier matrix having a reagent composition homogeneously incorporated therein, said reagent composition comprising a diazonium salt, an ester capable of being hydrolyzed in the presence of leukocyte, esterase or protease, and a salt of an alkaline earth metal.

16. The test device of claim 15, wherein said alkaline earth metal salt reduces background diazonium coupling and color change.

17. The test device of claim 15, wherein said composition additionally comprises an accelerator.

18. The test device of claim 17, wherein said accelerator is an alcohol having about 8–15 carbon atoms.

19. A method for determining the presence of an analyte selected from the group consisting of leukocytes, esterase or protease in a test sample, the method comprising: contacting the sample with a reagent composition or test device having said reagent composition homogeneously incorporated therein, said reagent composition comprising a diazonium salt, an ester capable of being hydrolyzed in the presence of leukocyte, esterase or protease, and a salt of an alkaline earth metal; and examining the reagent composition for a detectable response.

20. The method of claim 19, wherein said detectable response is chromogenic, fluorescent, a reflectance change, chemiluminescent, colorimetric or spectrophotometric.

21. The composition of claim 3 wherein said salt is $MgCl_2$.

* * * * *